(12) United States Patent
Kim et al.

(10) Patent No.: US 9,550,474 B2
(45) Date of Patent: Jan. 24, 2017

(54) INTEGRATED SENSOR APPARATUS OF VEHICLE

(71) Applicant: Hyundai Motor Company, Seoul (KR)

(72) Inventors: Hyun Sub Kim, Seoul (KR); Dae Hwan Kim, Daejeon (KR); Jin Hee Lee, Seoul (KR); Nak Kyoung Kong, Gyeonggi-Do (KR); Young Sub Oh, Gywonggi-Do (KR)

(73) Assignee: Hyundai Motor Company, Seoul (KR)

( * ) Notice: Subject to any disclaimer, the term of this patent is extended or adjusted under 35 U.S.C. 154(b) by 246 days.

(21) Appl. No.: 14/476,038

(22) Filed: Sep. 3, 2014

(65) Prior Publication Data
US 2015/0168299 A1 Jun. 18, 2015

(30) Foreign Application Priority Data
Dec. 17, 2013 (KR) .......................... 10-2013-0157425

(51) Int. Cl.
| | | |
|---|---|---|
| *B60S 1/08* | (2006.01) | |
| *G01N 21/94* | (2006.01) | |
| *G01N 21/958* | (2006.01) | |
| *G01N 21/55* | (2014.01) | |
| *G01N 21/552* | (2014.01) | |

(52) U.S. Cl.
CPC ............ *B60S 1/0837* (2013.01); *B60S 1/0844* (2013.01); *G01N 21/55* (2013.01); *G01N 21/552* (2013.01); *G01N 21/94* (2013.01); *G01N 21/958* (2013.01); *G01N 2021/945* (2013.01); *G01N 2021/9586* (2013.01)

(58) Field of Classification Search
CPC ..... B60S 1/0844; B60S 1/0833; B60S 1/0837; G01N 21/55; G01N 21/552; G01N 21/94; G01N 21/958; G01N 2021/551; G01N 2021/555; G01N 2021/556; G01N 2021/557; G01N 2021/558; G01N 2021/559; G01N 2021/945; G01N 2021/9586
See application file for complete search history.

(56) References Cited

U.S. PATENT DOCUMENTS

| | | | | |
|---|---|---|---|---|
| 4,867,561 A | * | 9/1989 | Fujii | ................. B60H 1/00785 15/DIG. 15 |
| 2014/0029008 A1 | * | 1/2014 | Hirai | ................... G01N 21/552 356/445 |

FOREIGN PATENT DOCUMENTS

| | | |
|---|---|---|
| JP | 2003-315256 A | 11/2003 |
| JP | 2009-042156 A | 2/2009 |

(Continued)

*Primary Examiner* — Gordon J Stock, Jr.
(74) *Attorney, Agent, or Firm* — Mintz Levin Cohn Ferris Glovsky and Popeo, P.C.; Peter F. Corless (57) ABSTRACT

An integrated sensor apparatus of a vehicle is provided that includes a light emitter that is configured to emit a light having an area of a predetermined range or greater to a first region of a windshield. A light receiver is configured to receive the light emitted by the light emitter and reflected from the first region of the windshield and an external light incident from the exterior to the windshield. Further, a light guider is configured to be attached to the windshield to guide the light emitted by the light emitter to be reflected from the first region of the windshield and arrive at the light receiver. An image sensor is configured to sense a plurality of image patterns from the light reflected by the first region of the windshield and the external light incident into the windshield from the exterior.

10 Claims, 8 Drawing Sheets

(56) References Cited

FOREIGN PATENT DOCUMENTS

| JP | 2009-092453 A | 4/2009 |
|----|---------------|--------|
| JP | 2010-190670 A | 9/2010 |
| JP | 2012-177576 A | 9/2012 |
| KR | 2012-0001922  | 1/2012 |
| KR | 10-2012-0012269 | 2/2012 |

* cited by examiner

INTEGRATED SENSOR APPARATUS OF VEHICLE

CROSS REFERENCE TO RELATED APPLICATION

This application is based on and claims priority from Korean Patent Application No. 10-2013-0157425, filed on Dec. 17, 2013 in the Korean Intellectual Property Office, the disclosure of which is incorporated herein in its entirety by reference.

BACKGROUND

Field of the Invention

The present invention relates to an integrated sensor apparatus and a method of a vehicle, and more particularly, to an integrated sensor apparatus implemented on a windshield.

Description of the Prior Art

A raindrop sensor that senses a raindrop state has been installed on vehicle windshields. The raindrop sensor is configured to sense the raindrop state (e.g., when rain contacts the windshield) by radiating light of a specific region and using an image of light reflected from the windshield. However, since the raindrop sensor according to the related art uses a point light, it has a substantially narrow raindrop sensing region on the windshield and it may be difficult to detect a thickness of water drop. In addition, an illumination sensor that senses an incident amount of external light to measure illumination has been installed on the windshield in the related art. However, when a plurality of sensors are disposed on the windshield of a vehicle, a sensor configuration becomes more complex and a manufacturing cost and other related costs increase.

SUMMARY

Accordingly, the present invention provides an integrated sensor apparatus of a vehicle configured to measure a raindrop state on a surface of a windshield and illumination for an external light incident through the windshield using an integrated single sensor. Particularly, the present invention provides an integrated sensor apparatus of a vehicle configured to measure a raindrop state by one region (e.g., a first region) and measure illumination by the other region (e.g., a second region) by dividing a sensing region of a single image sensor. Additionally, the present invention provides an integrated sensor apparatus of a vehicle configured to more easily measure a raindrop state on a surface of a windshield using a surface light.

In one aspect of the present invention, an integrated sensor apparatus of a vehicle may include: a light emitter configured to emit a light having an area of a predetermined range or greater to one region of a windshield; a light receiver configured to receive a light emitted by the light emitter and reflected from one region of the windshield and an external light incident from the exterior to the windshield; a light guider configured to be attached to the windshield to guide the light emitted by the light emitter to be reflected from one region of the windshield and arrive at the light receiver; and an image sensor configured to sense image patterns from the light reflected by one region of the windshield and the external light incident into the windshield from the exterior.

The image sensor may include a first sensing region configured to sense the image pattern from the light reflected by one region of the windshield and a second sensing region configured to sense an amount of the external light from the external light incident into the windshield from the exterior. The first sensing region may be a region that corresponds to a middle region of the windshield at which the light emitted by the light emitter arrives, among sensing regions of the image sensor, and the second sensing region may be regions that correspond to left and right side regions of the windshield at which the light emitted by the light emitter does not arrive.

The light receiver may include: a first light receiver configured to collect the light emitted by the light emitter and reflected by one region of the windshield and transfer the collected light to the first sensing region; and a second light receiver configured to collect the external light incident into the windshield from the exterior and transfer the collected external light to the second sensing region. The first light receiver may include: an object lens configured to concentrate the light reflected by one region of the windshield; and a reflecting plate configured to reflect the light concentrated by the object lens to arrive at the first sensing region of the image sensor.

The second light receiver may include: a light collector attached to the windshield to collect the external light incident into the windshield; an optical line connected to the second sensing region of the image sensor to transfer the external light collected by the light collector to the second sensing region of the image sensor; and a terminal configured to concentrate the external light collected by the light collector between the light collector and the optical line to guide the concentrated external light to the optical line. At least two light collectors may be provided and may be disposed in parallel on a surface of the windshield at a predetermined distance. The second light receiver may further include a blocking film disposed between the at least two light collectors to block interference of the external light which is each incident into the corresponding light collector. The light collector may be a photo-diode. The image sensor may be configured to sense a raindrop state on a surface of the windshield based on a change in illumination and the number of pixels of an image detected from the first sensing region. The image sensor may also be configured to sense illumination from a sum of the number of pixels of an image detected from the left side region of the second sensing region and the number of pixels of an image detected from the right side region of the second sensing region. Further, the image sensor may be configured to sense a morning time zone or an afternoon time zone according to a difference between the number of pixels sensed from the left side region of the second sensing region and the number of pixels sensed from the right side region of the second sensing region.

BRIEF DESCRIPTION OF THE DRAWINGS

The above and other objects, features and advantages of the present invention will be more apparent from the following detailed description taken in conjunction with the accompanying drawings, in which.

DETAILED DESCRIPTION

It is understood that the term "vehicle" or "vehicular" or other similar term as used herein is inclusive of motor vehicles in general such as passenger automobiles including sports utility vehicles (SUV), buses, trucks, various commercial vehicles, watercraft including a variety of boats and ships, aircraft, and the like, and includes hybrid vehicles, electric vehicles, combustion, plug-in hybrid electric vehicles, hydrogen-powered vehicles and other alternative fuel vehicles (e.g. fuels derived from resources other than petroleum).

Although exemplary embodiment is described as using a plurality of units to perform the exemplary process, it is understood that the exemplary processes may also be performed by one or plurality of modules. Additionally, it is understood that the term controller refers to a hardware device that includes a memory and a processor. The memory is configured to store the modules and the processor is specifically configured to execute said modules to perform one or more processes which are described further below.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/of" includes any and all combinations of one or more of the associated listed items.

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Hereinafter, the present invention will be described in detail with reference to the accompanying drawings. In particular, like reference numerals denote like elements in the drawings. In addition, a detailed description of the function and/or the configuration already known in the art will be omitted. Hereinafter, portions necessary to understand operations according to various exemplary embodiments of the present invention are mainly described and a description of elements which may obscure a gist of the description will be omitted. In addition, some components shown in the drawings are exaggerated, omitted or schematically illustrated. The size of each component does not exactly reflect its real size, and accordingly, the contents described herein are not limited by a relative size or an interval of the components drawn in the respective drawings.

Figure 1:
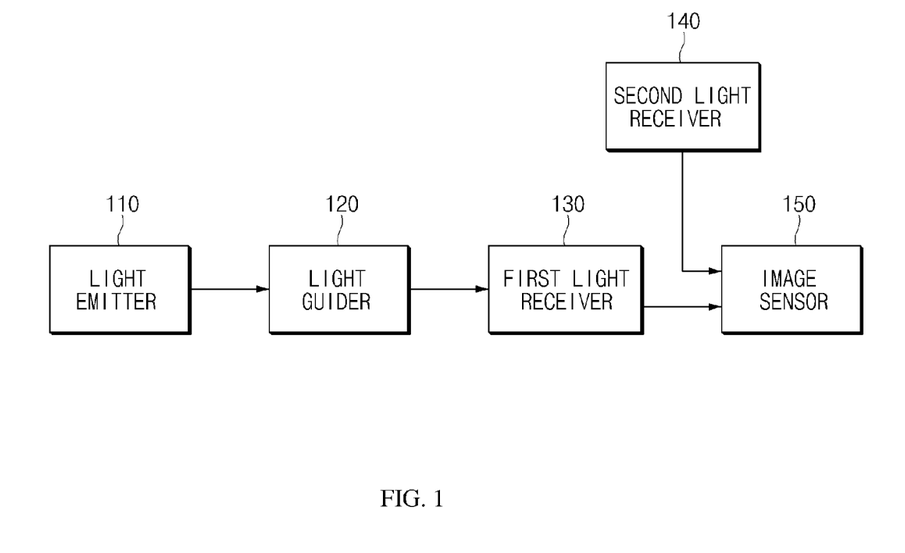
FIG. 1 is an exemplary diagram showing a configuration of an integrated sensor apparatus of a vehicle according to an exemplary embodiment of the present invention.

FIG. 1 is an exemplary diagram showing an integrated sensor apparatus of a vehicle according to an exemplary embodiment of the present invention. Referring to FIG. 1, the integrated sensor apparatus of the vehicle according to the exemplary embodiment of the present invention may include a light emitter 110, a light guider 120, a light receiver and an image sensor 150. In addition, the light receiver may include a first light receiver 130 configured to receive a light emitted by the light emitter 110 and a second light receiver 140 configured to receive an external light.

First, the light emitter 110 may be configured to emit the light having an area of a predetermined range or greater onto one region of a windshield 10. In particular, the light emitter 110 may correspond to a back light unit (BLU) configured to emit a surface light. One region of the windshield 10, which may be a region that defines a front sight of a vehicle passenger, for example, a driver, may be about a middle region of the windshield 10 that may disturb or block a sight of the driver based on a raindrop state. Therefore, an exemplary embodiment of the present invention in which the light emitter 110 is applied to the windshield 10 will be described with reference to FIG. 2.

The light guider 120 may be installed to be attached to one surface of the windshield 10 and may be formed to cause the surface light emitted by the light emitter 110 to be reflected from the windshield 10. In particular, the light guider 120 may be formed of a prism. In addition, the light guider 120 may be configured to guide the light reflected from one region of the windshield 10 to arrive at the light receiver when the surface light emitted by the light emitter 110 is reflected from one region of the windshield 10. The first light receiver 130 may be configured to receive the surface light emitted by the light emitter 110 and reflected from one region of the windshield 10 through the light guider 120. In particular, the first light receiver 130 may be configured to collect the light transferred through the light guider 120 and transfer the collected light to the image sensor 150. A detail structure of the first light receiver 130 will be described with reference to FIG. 3.

Figure 3:
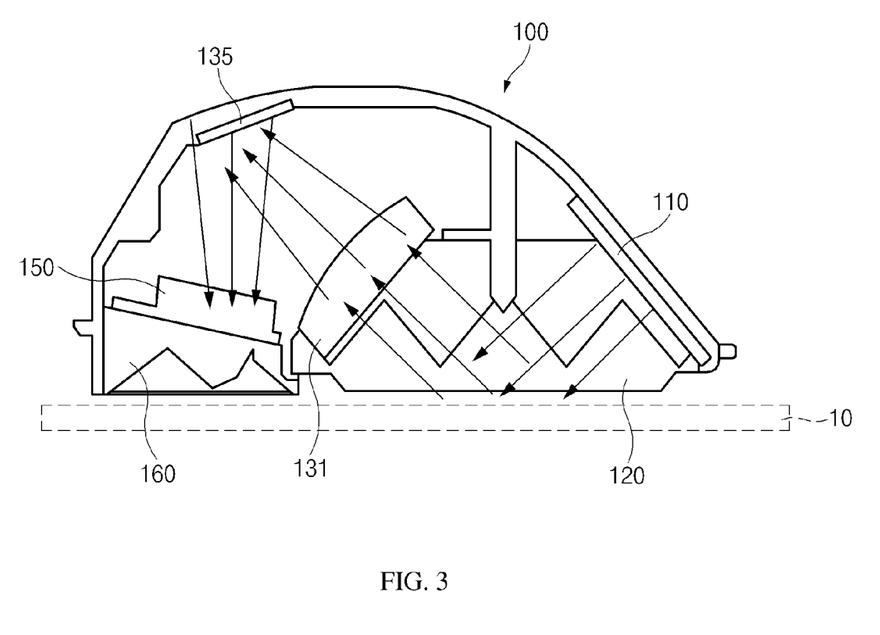

As shown in FIG. 3, the first light receiver 130 may include an object lens 131 and a reflecting plate 135. The object lens 131 may be configured to concentrate the light reflected from one region of the windshield 10 and transferred through the light guider 120. In particular, the light concentrated by the object lens 131 may pass through the object lens 131 and may then be transferred to the reflecting plate 135. The reflecting plate 135 may be configured to reflect the light passing through the object lens 131 to arrive at the image sensor 150. In particular, the light reflected from the reflecting plate 135 may arrive at a first sensing region of the image sensor 150 as described below.

The second light receiver 140 may be configured to collect the external light which is incident into the windshield 10 from the exterior and passes through the windshield 10. The second light receiver 140 may be configured to transfer the collected external light to a second sensing region of the image sensor. Particularly, the external light which is incident from the exterior and passes through the windshield 10 may be solar light. Therefore, a detail structure of the second light receiver 140 will be described with reference to FIG. 5.

Figure 5:
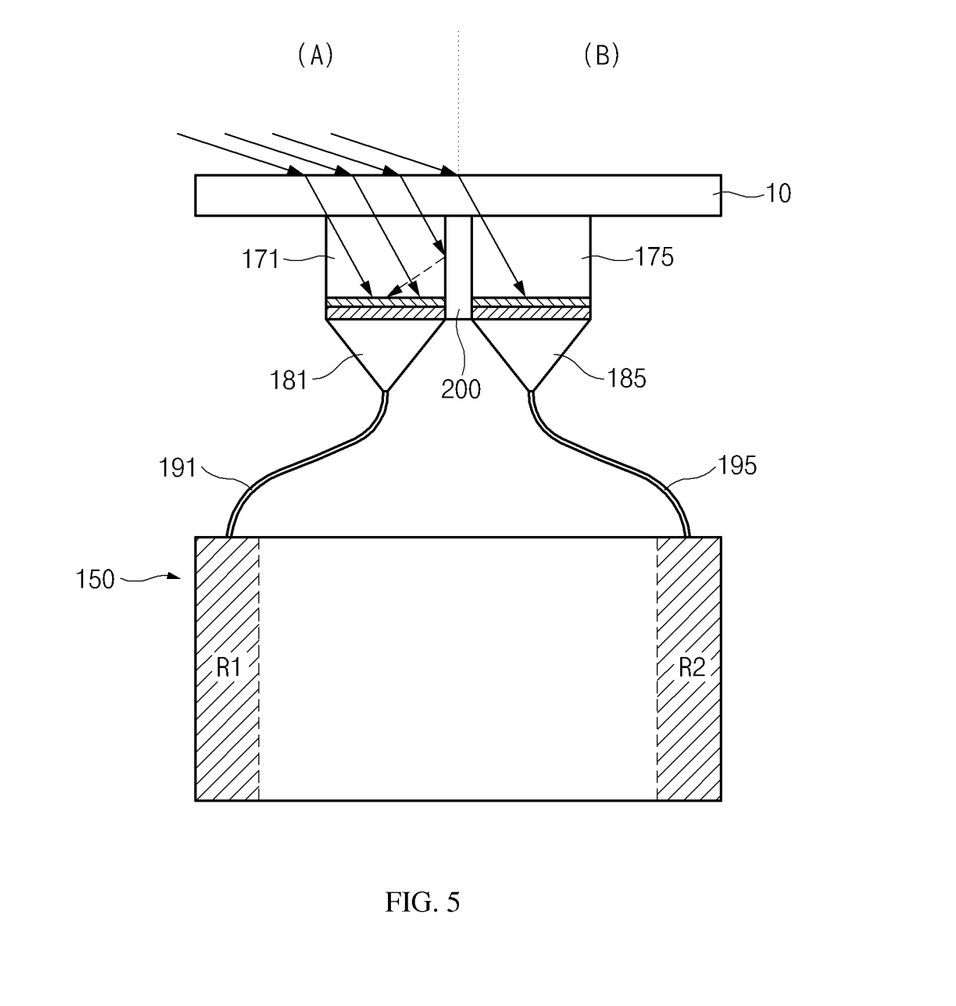
FIGS. 5 and 6 are exemplary reference diagrams for describing an operation of sensing illumination by a windshield sensing apparatus according to the exemplary embodiment of the present invention.

As shown in FIG. 5, the second light receiver 140 may include light collectors 171 and 175, terminals 181 and 185, and optical lines 191 and 195. The light collectors 171 and 175 may be installed to be attached onto one surface of the windshield 10 to collect the external light passing through the windshield 10 from the exterior. As an example, the light collectors 171 and 175 may be a photo-diode. In addition, at least two light collectors 171 and 175 may be provided and disposed in parallel on one surface of the windshield 10 at a predetermined distance from each other from the left to right directions. In particular, the second light receiver 140 may further include a blocking film disposed between the at least two light collectors 171 and 175 to block interference between the external light sources incident into the respective light collectors 171 and 175. The blocking film may be made of a material through which light is not able to transmit.

The external light sources collected by the light collectors 171 and 175 may be concentrated on the terminals 181 and 185. In particular, the external light sources concentrated on the terminals 181 and 185 may be transferred to a second sensing region by the optical lines 191 and 195 transferring the concentrated external light sources to the terminals 181 and 185 between the terminals 181 and 185 and the second sensing region of the image sensor 150. Further, the external light collected by the light collector 171 disposed at the left side may be transferred to a left side region of the second sensing region and the external light collected by the light collector 175 disposed at the right side may be transferred to a right side region of the second sensing region.

The image sensor 150 may be configured to sense an image pattern from the surface light reflected by one region of the windshield 10 and the external light incident into the windshield 10. In particular, the image sensor 150 may include a first sensing region that senses the image pattern from the surface light reflected by one region of the windshield 10 and a second sensing region that senses an amount of the external light from the external light incident from the exterior and passing through the windshield 10.

Specifically, the first sensing region may be a region that corresponds to about a middle region of the windshield 10 at which the surface light emitted by the light emitter 110 arrives, among sensing regions of the image sensor 150. Therefore, the image sensor 150 may be configured to sense the image pattern of the surface light arrived at the first sensing region by the first light receiver 130. In addition, since the image pattern may be varied based on the raindrop state on the surface of the windshield 10, the image sensor 150 may be configured to sense the raindrop state from the image pattern sensed from the first sensing region.

Furthermore, the second sensing region may be a region that corresponds to left and right side regions of the windshield 10 at which the surface light emitted by the emitter 110 does not arrive (e.g., the light does not reach this region or area, the light is not emitted toward the left and right side regions). In particular, the second sensing region at which the surface light does not arrive may be connected to the optical lines 191 and 195 of the second light receiver 140, to transfer the external light collected by the light receiver through the optical lines 191 and 195. The external light collected by the light collector 171 provided to the left side of the second light receiver 140 may be transferred to the left side region of the second sensing region through the optical line connected to the left side region of the second sensing region. Meanwhile, the external light collected by the light collector 175 provided to the right side of the second light receiver 140 may be transferred to the right side region of the second sensing region through the optical line connected to the right side region of the second sensing region.

Figure 2:
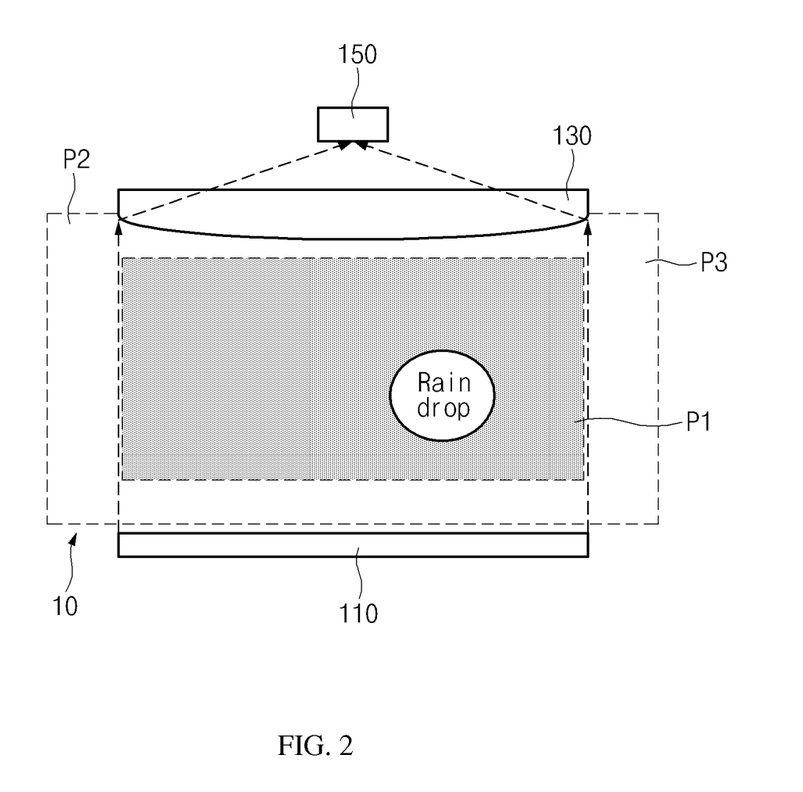
FIGS. 2 to 4 are exemplary reference diagrams for describing an operation of sensing a raindrop state by the integrated sensor apparatus of the vehicle according to the exemplary embodiment of the present invention.
Figure 4:
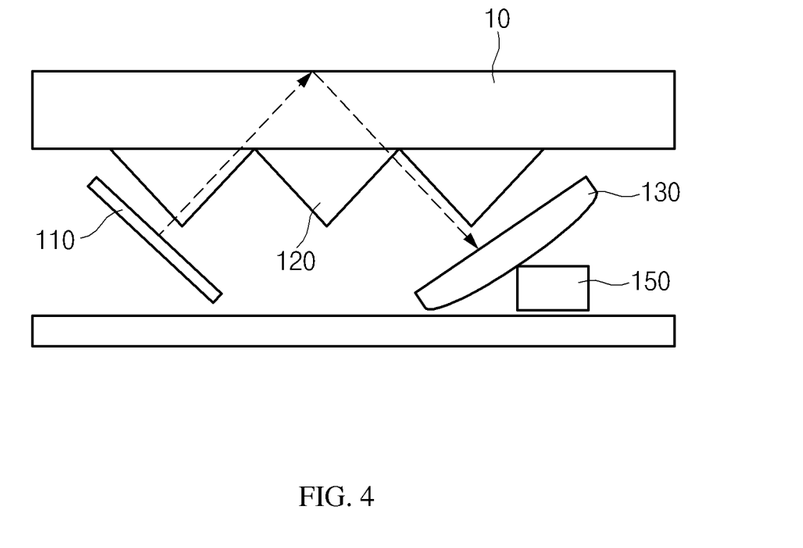

FIGS. 2 to 4 are exemplary reference diagrams for describing an operation of sensing a raindrop state by the integrated sensor apparatus of the vehicle according to the exemplary embodiment of the present invention. First, FIG. 2 shows an exemplary arrangement structure of the light emitter and the image sensor on the windshield. As shown in FIG. 2, the light emitter 110 may be configured to emit the surface light having an area of a predetermined range or greater to one region P1 of the windshield 10 (e.g., a first region P1) to sense the raindrop state of a wide region. In particular, one region P1 of the windshield 10 may be about a middle region of the windshield 10 as shown in FIG. 2. As an example, one region P1 of the windshield 10 may be a region that includes about a middle region except for about a 10% region P2 of the left side and about a 10% region P3 of the right side. Of course, a range for one region P1 of the windshield 10 is not limited to any one range.

In addition, the light emitter 110 may be implemented to have about the same length as one region P1 of the windshield 10 based on a horizontal direction of the windshield 10. The surface light emitted by the light emitter 110 may be reflected from one region P1 of the windshield 10 by the light guider 120, may pass through the object lens 131 provided at a side opposite to the light emitter 110, and may arrive at (e.g., reach) the first sensing region of the image sensor 150. As shown in FIG. 2, when water drops have been formed on a portion of one region P1 of the windshield 10, reflection patterns of the light in the corresponding region may be different. Therefore, since the reflection patterns arriving at the image sensor 150 may be different, the image pattern having different shapes may be detected from a position on which the water drop is formed.

FIGS. 3 and 4, which show an exemplary sensor structure for the integrated sensor apparatus of the vehicle according to the exemplary embodiment of the present invention, show an exemplary transfer path of the surface light. As shown in FIGS. 3 and 4, in the integrated sensor apparatus 100 of the vehicle, when the surface light is emitted by light emitter 110 to the light guider 120 formed to be attached to the windshield 10, the emitted surface light may be reflected from the windshield 10 by the light guider 120 and may arrive at the object lens 131 of the first light receiver 130. In particular, the object lens 131 may filter and pass through the transferred surface light, and the surface light passing through the object lens 131 may be reflected by the reflecting plate 135 to be arrived at the image sensor 150.

The surface light may be refracted by the reflecting plating 135 to arrive at the first sensing region of the image sensor 150, to increase a focal distance. In particular, as the focal distance is increased, an in-depth image pattern for the water drop on the windshield 10 may be detected. Therefore, the image sensor 150 may be configured to detect the image pattern of the surface light reflected from one region of the windshield 10 and may be configured to detect the raindrop state from the detected image pattern. Meanwhile, the integrated sensor apparatus of the vehicle according to the exemplary embodiment of the present invention may further include a jointer 160 configured to fix the integrated sensor apparatus of the vehicle on the windshield.

Figure 6:
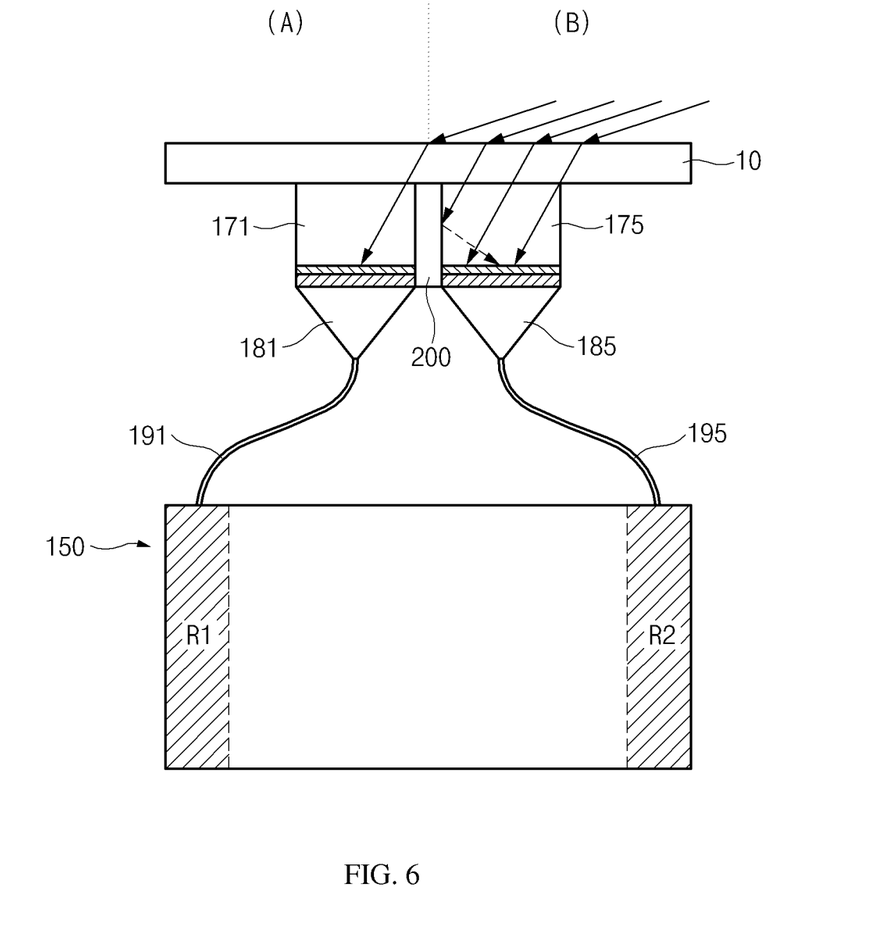
Figure 7A:
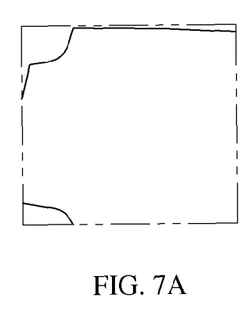
FIGS. 7A-7E and 8A-8B are exemplary diagrams showing results measured by an image sensor applied to the integrated sensor apparatus of the vehicle according to the exemplary embodiment of the present invention.
Figure 7B:
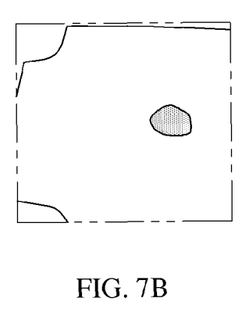
Figure 7C:
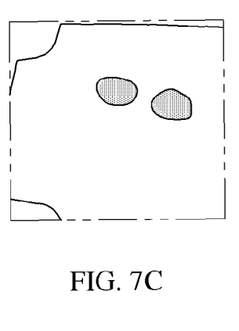
Figure 7D:
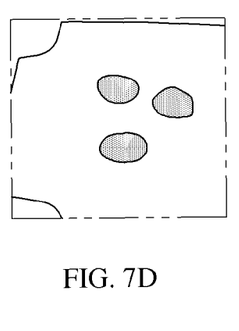
Figure 7E:
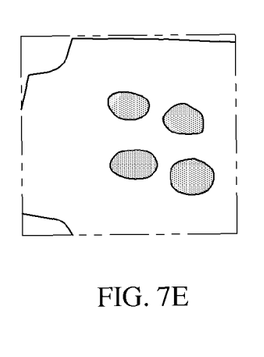

FIGS. 5 and 6 are exemplary reference diagrams for describing an operation of sensing illumination by the integrated sensor apparatus of the vehicle according to the exemplary embodiment of the present invention. FIG. 5 shows the external light incident into the windshield 10 from a left side A direction to a right side B direction and FIG. 6 shows the external light incident into the windshield 10 from the right side B direction to the left side A direction.

As shown in FIGS. 5 and 6, an incident direction of the external light into the windshield 10 may be varied depending on a position of the external light. In other words, the external light may be incident into the windshield 10 from (A) to (B) direction ((A)→(B) direction) and may be incident into the windshield 10 from (B) to (A) direction ((B)→(A) direction). In particular, a difference in light amount received at the light collectors 171 and 175 respectively provided at the left side and the right side of the windshield 10 may be generated depending on the incident direction of the external light.

a blocking film 200 may be disposed between the at the light collectors 171 and 175 to block interference of the external light which is each incident into the light collectors 171 and 175. As an example, as shown in FIG. 5, when the external light is incident in the (A)→(B) direction, the external light collected by the light collector 171 of the left side may be concentrated on the terminal 181 of the left side and may be transferred to a left side region R1 of the second sensing region of the image sensor 150 along the optical line 191 of the left side. Meanwhile, the external light collected by the light collector 175 of the right side may be concentrated on the terminal 185 of the right side and may be transferred to a right side region R2 of the second sensing region of the image sensor 150 along the optical line 195 of the right side.

Further, a greater amount of external light may be collected by the light collector 171 of the left side depending on the incident direction of the external light. Therefore, the greater amount of external light may be transferred to the R1. In particular, the number of pixels of the image pattern detected from the R1 becomes greater than that of the image pattern detected from the R2. The image sensor 150 may be configured to sense illumination from a sum of the number of pixels detected from the R1 and the number of pixels detected from the R2 and may be configured to sense a morning or an afternoon time frame according to a variation in the pixels between the R1 and the R2.

As another example, as shown in FIG. 6, when the external light is incident in the (B)→(A) direction, the external light collected by the light collector 171 of the left side may be concentrated on the terminal 181 of the left side and may be transferred to a left side region R1 of the second sensing region of the image sensor 150 along the optical line 191 of the left side. Meanwhile, the external light collected by the light collector 175 of the right side may be concentrated on the terminal 185 of the right side and may be transferred to a right side region R2 of the second sensing region of the image sensor 150 along the optical line 195 of the right side.

In particular, a greater amount of external light may be collected by the light collector 175 of the right side depending on the incident direction of the external light. Therefore, the greater amount of external light may be transferred to the R2. The number of pixels of the image pattern detected from the R2 becomes greater than that of the image pattern detected from the R1. The image sensor 150 may be configured to sense illumination from a sum of the number of pixels detected from the R1 and the number of pixels detected from the R2 and may be configured to sense a morning or an afternoon condition according to a variation in the pixels between the R1 and the R2.

When the image pattern detected from the R1 and the R2 in the exemplary embodiment of FIG. 5 is the image pattern of a morning time zone, the image pattern detected from the R1 and the R2 in the exemplary embodiment of FIG. 6 may be the image pattern of the afternoon time zone, or vice versa. Further, the arrangement positions of the light collectors 171 and 175 shown in FIGS. 5 and 6 correspond to an exemplary embodiment of the present invention, and the arrangement position may be changed according to the exemplary embodiment of the present invention.

FIGS. 7A-7E are diagrams showing examples for measurement images measured by an image sensor applied to the integrated sensor apparatus of the vehicle according to the exemplary embodiment of the present invention. Referring to the images of FIG. 7A to 7E, these images show results obtained by detecting the images for the surface light reflected from one region of the windshield. The images shown in FIG. 7A to 7E are detected over about 60 times per 1 second by the image sensor and the pattern of the water drop in the images shown in FIG. 7A to 7E may be detected to change according to a time variation. In particular, the image sensor may be configured to detect the change in illumination and the number of pixels from the images shown in FIG. 7A to 7E to detect the pattern of the water drop. Therefore, the change in the illumination and the number of pixels detected form the image for the surface light is as shown in FIGS. 8A-8B.

Figure 8A:
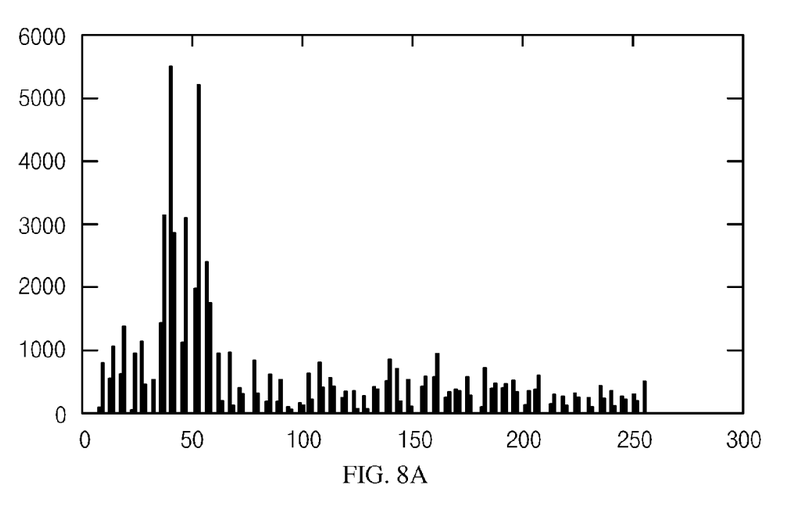
Figure 8B:
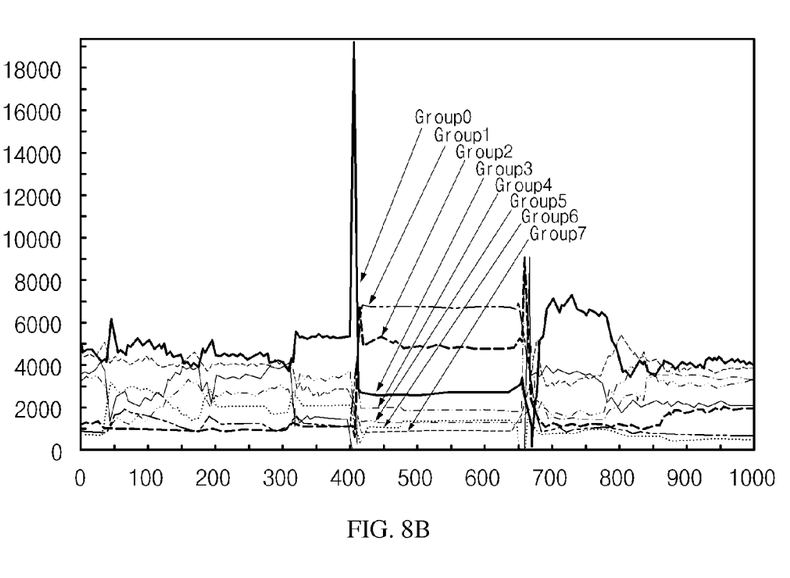

FIGS. 8A-8B are exemplary diagrams showing results measured using the image sensor applied to the integrated sensor apparatus of the vehicle according to the exemplary embodiment of the present invention. FIG. 8A shows the results obtained by detecting the change in the illumination and the number of pixels from an image detected at a specific time and FIG. 8B shows the results obtained by detecting the change in the illumination and the number of pixels an image detected for each of the different times (e.g., predetermined time intervals).

According to the exemplary embodiment of the present invention, the raindrop state may be measured through one region (e.g., a first region) and illumination may be measured through the other region (e.g., a second region) by dividing the sensing region of the single image sensor, to allow the integrated single sensor to implemented to solve a cost problem and a space application problem caused in applying a plurality of sensors. In addition, according to the exemplary embodiment of the present invention, the raindrop state on the surface of the windshield may be measured using the surface light, to more easily detect the raindrop state on the surface of the windshield having the wider area.

The spirit of the present invention has been just exemplified. It will be appreciated by those skilled in the art that various modifications and alterations may be made without departing from the essential characteristics of the present invention. Accordingly, the exemplary embodiments disclosed in the present invention and the accompanying drawings are used not to limit but to describe the spirit of the present invention. The scope of the present invention is not limited only to the exemplary embodiments and the accompanying drawings. The protection scope of the present invention must be analyzed by the appended claims and it should be analyzed that all spirits within a scope equivalent thereto are included in the appended claims of the present invention.

What is claimed is:

1. An integrated sensor apparatus of a vehicle, comprising:
   a light emitter configured to emit a light having an area of a predetermined range to a first region of a windshield;
   a light receiver configured to receive the light emitted by the light emitter and reflected from the first region of the windshield and an external light incident from the exterior to the windshield;
   a light guider configured to be attached to the windshield to guide the light emitted by the light emitter to be reflected from the first region of the windshield and arrive at the light receiver; and an image sensor configured to sense a plurality of image patterns from the light reflected by the first region of the windshield and the external light incident into the windshield from the exterior, wherein the image sensor includes a first sensing region configured to sense the image pattern from the light reflected by the first region of the windshield and a second sensing region configured to sense amount of the external light from the external light incident into the windshield from the exterior, and wherein the first sensing region is a region that corresponds to a substantially middle region of the windshield at which the light emitted by the light emitter arrives, among the sensing regions of the image sensor, and the second sensing region is regions that correspond to left and right side regions of the windshield where the light emitted by the light emitter does not arrive.

2. The integrated sensor apparatus according to claim 1, wherein the image sensor is configured to sense a raindrop state on a surface of the windshield based on a change in illumination and the number of pixels of an image detected from the first sensing region.

3. The integrated sensor apparatus according to claim 1, wherein the image sensor is configured to sense illumination from a sum of the number of pixels of an image detected from the left side region of the second sensing region and the number of pixels of an image detected from the right side region of the second sensing region.

4. The integrated sensor apparatus according to claim 1, wherein the image sensor is configured to sense a morning time zone or an afternoon time zone based on a difference between the number of pixels sensed from the left side region of the second sensing region and the number of pixels sensed from the right side region of the second sensing region.

5. The integrated sensor apparatus according to claim 1, wherein the light receiver includes:

a first light receiver configured to collect the light emitted by the light emitter and reflected by the first region of the windshield and configured to transfer the collected light to the first sensing region; and a second light receiver configured to collect the external light incident into the windshield from the exterior and configured to transfer the collected external light to the second sensing region.

6. The integrated sensor apparatus according to claim 5, wherein the first light receiver includes:

an object lens configured to concentrate the light reflected by the first region of the windshield; and a reflecting plate configured to reflect the light concentrated by the object lens to arrive at the first sensing region of the image sensor.

7. The integrated sensor apparatus according to claim 5, wherein the second light receiver includes:

a light collector attached to the windshield to collect the external light incident into the windshield;

an optical line connected to the second sensing region of the image sensor to transfer the external light collected by the light collector to the second sensing region of the image sensor; and a terminal configured to concentrate the external light collected by the light collector between the light collector and the optical line to guide the concentrated external light to the optical line.

8. The integrated sensor apparatus according to claim 7, wherein the light collector is a photo-diode.

9. The integrated sensor apparatus according to claim 7, wherein at least two light collectors are provided and disposed in parallel on a surface of the windshield at a predetermined distance.

10. The integrated sensor apparatus according to claim 9, wherein the second light receiver further includes:

a blocking film disposed between the at least two light collectors to block interference of the external light which is each incident into the corresponding light collector.

* * * * *